US00PP29908P2

(12) United States Plant Patent
Van Swieten

(10) Patent No.: US PP29,908 P2
(45) Date of Patent: Nov. 27, 2018

(54) ***PHALAENOPSIS* ORCHID PLANT NAMED 'PHALGONDAL'**

(50) Latin Name: ***Phalaenopsis* hybrid**
Varietal Denomination: PHALGONDAL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,847

(22) Filed: Aug. 14, 2017

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGONDAL', particularly characterized by having white flowers, 1 to 6 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGONDAL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGONDAL'.

The new *Phalaenopsis* plant is a product of a planned breeding program conducted by the inventor in Bleiswijk, The Netherlands. The objective of this breeding program was to create a new *Phalaenopsis* plant with numerous stalks and attractive white flowers suitable for potted plant production.

The new *Phalaenopsis* plant 'PHALGONDAL' is a result of cross-pollination made by the inventor in July 2008 in Bleiswijk, The Netherlands of the proprietary female, or seed parent, *Phalaenopsis* hybrid '01-3120' (unpatented) with the proprietary male, or pollen parent, *Phalaenopsis* hybrid '22444-010' (unpatented).

The new *Phalaenopsis* was selected by the inventor as a single plant within the progeny of the stated cross-pollination in a controlled greenhouse in Bleiswijk, The Netherlands in August 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGONDAL' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGONDAL' as a new and distinct variety of *Phalaenopsis* plant.

1) Flower is white;
2) 1 to 6 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in June 2017. Colors in the photographs may differ from the color values cited in the detailed botanical description, which accurately describe the actual colors of the new variety.

DESCRIPTION OF THE NEW VARIETY

Figure 1:
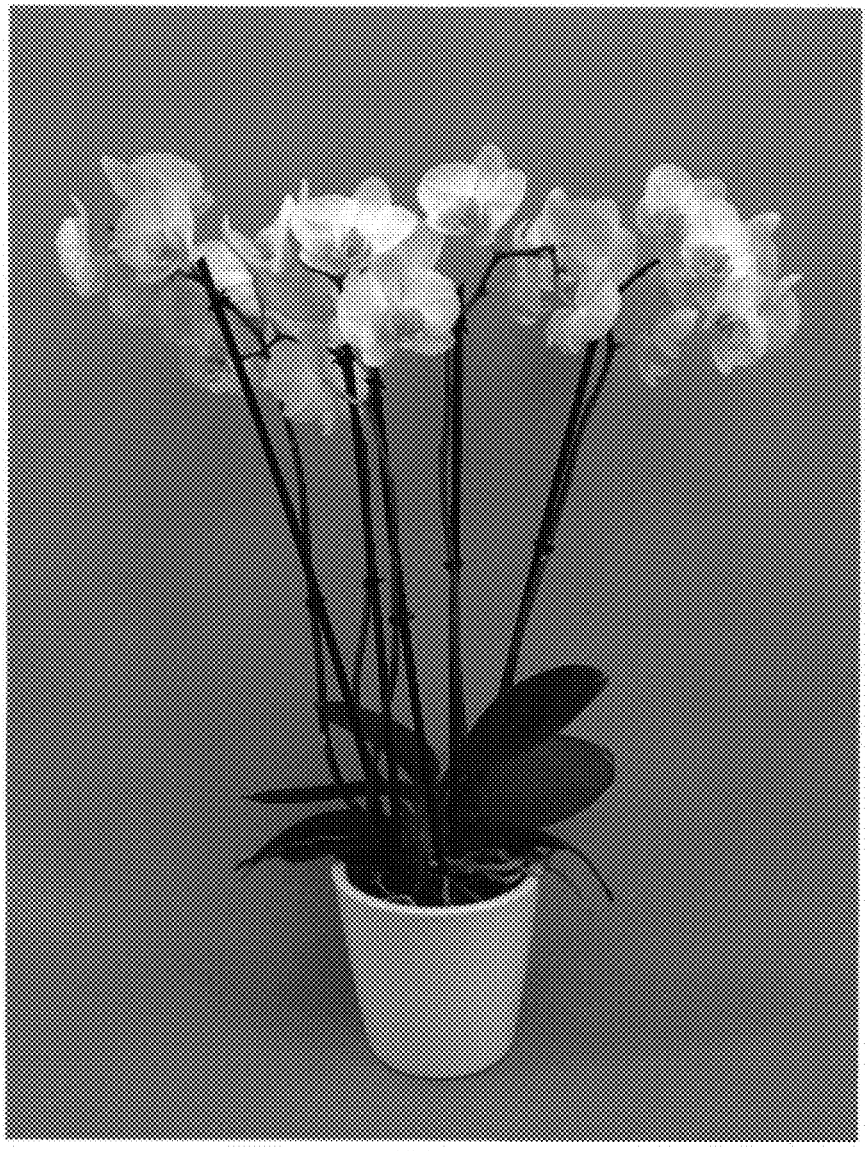
FIG. 1 shows the overall plant habit, including blooms and foliage of 'PHALGONDAL'.
Figure 2:
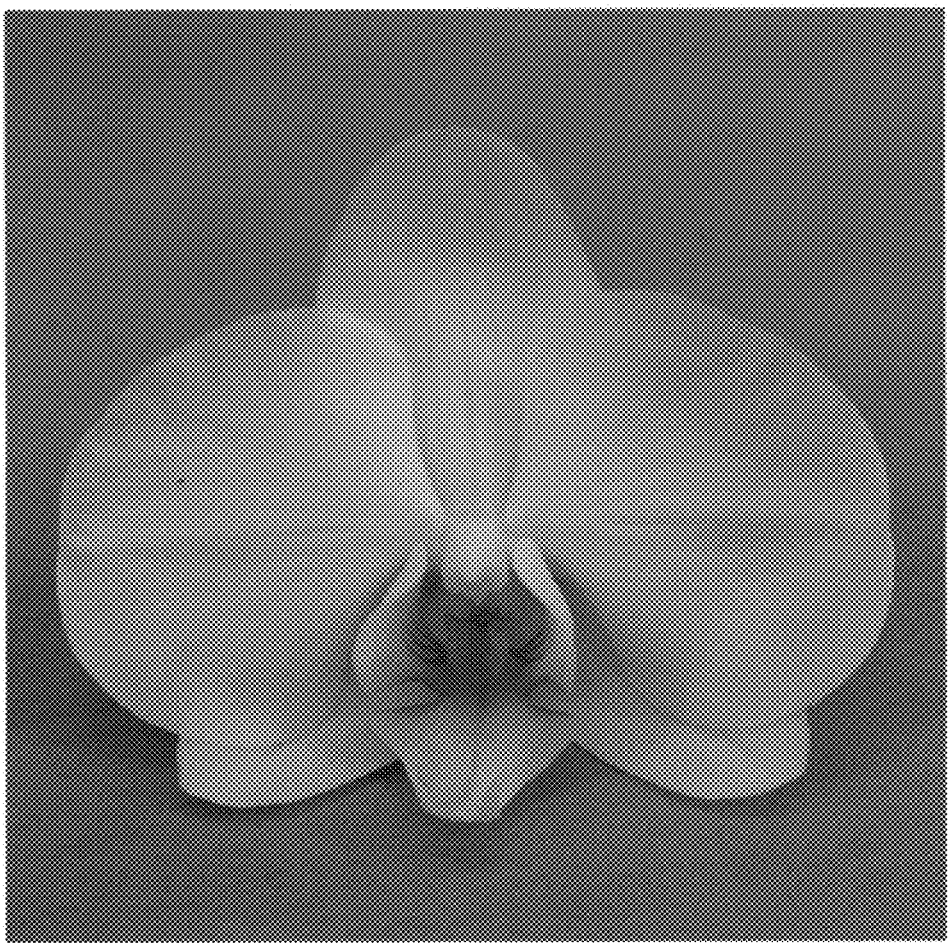
FIG. 2 shows a close-up of a flower of 'PHALGONDAL'.
Figure 3:
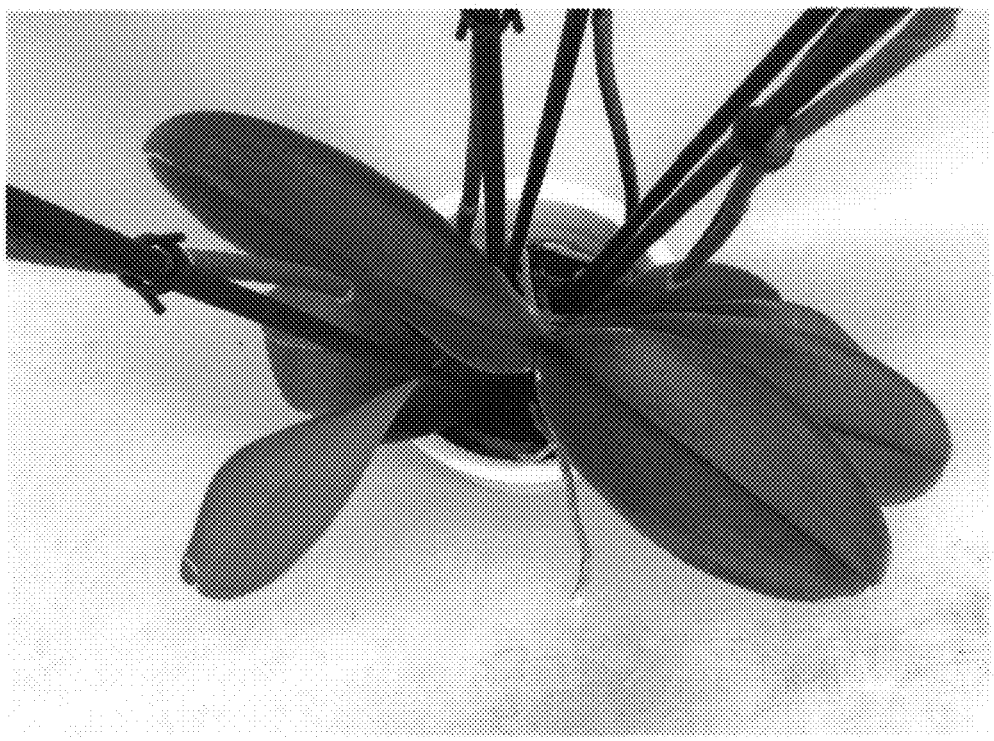
FIG. 3 shows a close-up of the leaves of 'PHALGONDAL'.

The following detailed description sets forth the distinctive characteristics of 'PHALGONDAL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in June 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGONDAL'.

Parentage:

*Female parent*.—*Phalaenopsis* cultivar '01-3120' (unpatented).

*Male parent*.—*Phalaenopsis* cultivar '22444-010' (unpatented).

Propagation:

*Type*.—Meristem tissue culture.

Roots:

*Root description*.—Light green colored roots (RHS 146B) with branching lateral roots having light green colored root tips (RHS 146C).

Plant:

*Commercial crop time to flowering*.—Approximately 48 to 50 weeks from a rooted cutting to finish in a 12 cm pot.

*Growth habit of peduncle*.—Standard, green leaves, raceme.

*Height (from soil level to top of inflorescence)*.—Approximately 50.0 cm to 55.0 cm.

*Width (measured from leaf tips)*.—About 29.0 cm to 31.0 cm.

*Vigor*.—Moderate.

Leaves:

*Mature leaves*.—Quantity per plant: 9 to 11 leaves are produced before flowering. Length (fully expanded): 14.5 cm to 16.5 cm. Width: 6.0 cm to 7.0 cm. Shape: Oblong. Base shape: Moderately elongated. Apex: Obtuse unequal. Leaf blade angle with the petiole (measured from the horizontal position): Between 10 degrees and 25 degrees. Leaf margin: Entire. Color: Upper surface: RHS 146A. Lower surface: RHS 146B. Texture: Rough. Thickness: 2.2 mm to 2.5 mm. Venation: Pattern: Parallel. Color of the midvein: Upper surface: RHS 146A. Lower surface: RHS 146B.

Peduncle:

*Quantity per plant*.—1 to 6.

*Number of flowers per peduncle*.—6 to 10.

*Length*.—39.0 cm to 54.0 cm.

*Diameter*.—5.0 mm to 5.5 mm.

*Strength*.—Moderate.

*Aspect*.—Upright to slightly pendant.

*Texture*.—Smooth.

*Color*.—Green (RHS 144A) with a touch of light brown (RHS N199A) at the base.

*Internode length*.—4.0 cm to 5.0 cm.

*Callosities*.—None.

Inflorescence description:

*Appearance*.—Upright to slightly pendant, raceme inflorescence with bilaterally symmetrical flowers that open in succession beginning with the lowermost flower.

*Inflorescence size*.—Height (from base to tip): 120.0 mm to 150.0 mm.

*Flowering time*.—First flowers can be expected 10 to 11 months after planting in a 12 cm (diameter) pot.

*Flower*.—Height: 60.0 mm to 65.0 mm. Diameter: 78.0 mm to 83.0 mm. Depth of lip: 22.0 mm to 24.0 mm.

*Flower longevity*.—On the plant: 11 to 21 weeks.

*Fragrance*.—Absent.

*Flower bud*.—Average size: Large. Length: 22.0 mm to 24.0 mm. Width: 17.0 mm to 19.0 mm. Shape: Egg shaped. Color: Light green (RHS 145C) and diluting light red-purple (RHS 184C).

*Petals*.—Arrangement: Open/free. Shape: Semi-circular. Apex: Rounded asymmetric. Margin: Slightly undulated. Length (from base to tip): 37.0 mm to 39.0 mm. Width: 45.0 mm to 47.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptic. Apex: Rounded to slightly emarginated. Margin: Entire. Length (from base to tip): 41.0 mm to 43.0 mm. Width: 30.0 mm to 32.0 mm. Color (when fully opened): Upper surface: Basic color: White (RHS NN155C). Over color: Absent. Lower surface: Basic color: White (RHS NN155C). Over color: Light purple (RHS 76B).

*Lateral sepals*.—Shape: Ovate. Apex: Obtuse asymmetric. Margin: Entire. Length (from base to tip): 38.0 mm to 40.0 mm. Width: 26.0 mm to 28.0 mm. Color (when fully opened): Upper surface: Basic color: White (RHS NN155C). Over color: Light purple (RHS N78D) at the base. Lower surface: Basic color: White (RHS NN155C). Over color: Light purple (RHS 76B).

*Labellum (lip)*.—Whiskers: Present. Length of whiskers: 19.0 mm to 21.0 mm. Color of whiskers: White (RHS NN155C) at the base and yellow (RHS 8B) toward the tips. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 20.0 mm to 22.0 mm. Width: 14.0 mm to 16.0 mm. Color: White (RHS NN155C) with few red-purple (RHS 64A) stripes at the base and yellow (RHS 9B) on one side.

*Apical lobe*.—Shape: Triangular. Margin: Entire. Length: 19.0 mm to 21.0 mm. Width: 23.0 mm to 25.0 mm. Color: Yellow at the base and stripe in the middle (RHS 9B/C); light brown (RHS 172B) on the side of wings and white (RHS NN155C) toward the whiskers.

*Callus*.—Average size: Medium. Height: 6.0 mm to 7.0 mm. Length: 6.0 mm to 7.0 mm. Width: 4.0 mm to 5.0 mm. Color: Yellow (RHS 9C) dotted (RHS 172A).

Reproductive organs:

*Column*.—Length: 8.0 mm to 10.0 mm. Diameter: 6.0 mm to 6.3 mm. Color: White (RHS NN155C).

*Pollinia*.—Quantity: 2. Diameter: 1.0 mm to 1.2 mm. Color: Orange (RHS 25A).

*Ovary*.—Length: 8.0 mm to 10.0 mm. Diameter: 2.3 mm to 2.5 mm.

*Pedicel*.—Length: 31.0 mm to 33.0 mm. Diameter: 2.7 mm to 2.9 mm. Color: Green (RHS 145B/C) at the base and slightly light purple (RHS 76B) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL LINES AND MOST SIMILAR VARIETIES

'PHALGONDAL' differs from female parent plant '01-3120' (unpatented) in that 'PHALGONDAL' has red-purple stripes on the lateral lobe, green peduncles with a touch of light brown at the base and lateral sepals with an over color, whereas '01-3120' has dark red stripes on the lateral lobe, peduncles with a mix of light green and light brown and lateral sepals with no over color. Additionally, 'PHALGONDAL' has smaller flowers than '01-1320'.

'PHALGONDAL' differs from male parent plant '22444-010' (unpatented) in that 'PHALGONDAL' has red-purple (RHS 64A) stripes on the lateral lobe, green peduncles with a touch of light brown at the base and lateral sepals with an over color, whereas '22444-010' has red-purple (RHS 70A/B) stripes on the lateral lobe, green peduncles and lateral sepals with no over color. Additionally, 'PHALGONDAL' has narrower apical lobes than '22444-010'.

'PHALGONDAL' is most similar to the commercial *Phalaenopsis* plants named 'PHALZIFY' (unpatented) and 'PHALUBIEN' (unpatented). 'PHALGONDAL' differs from the commercial variety 'PHALZIFY' in that 'PHALGONDAL' has light purple over color on the lateral sepals, green peduncles with a touch of light brown at the base and medium curvature of the lateral lobes, whereas 'PHALZIFY' has no over color on the lateral sepals, green peduncles and strong curvature of the lateral lobes. Additionally, 'PHALGONDAL' has smaller flowers and slightly longer whiskers than 'PHALZIFY'.

'PHALGONDAL' differs from the commercial variety 'PHALUBIEN' in that 'PHALGONDAL' has light purple over color on the lateral sepals and green peduncles with a touch of light brown at the base, whereas 'PHALUBIEN' has light green over color on the lateral sepals and peduncles with a mix of dark green and brown. Additionally, 'PHALGONDAL' has smaller flowers and longer whiskers than 'PHALUBIEN'.

I claim:

1. A new and distinct variety of *Phalaenopsis* plant named 'PHALGONDAL', substantially as described and illustrated herein.

* * * * *